United States Patent
Takaai et al.

(10) Patent No.: US 8,420,752 B2
(45) Date of Patent: Apr. 16, 2013

(54) PRODUCTION METHOD AND PRODUCTION APPARATUS OF PARTICULATE WATER ABSORBING AGENT CONTAINING WATER ABSORBENT RESIN AS MAIN COMPONENT

(75) Inventors: Toshihiro Takaai, Hyogo (JP); Yorimichi Dairoku, Okayama (JP); Shinichi Fujino, Hyogo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 364 days.

(21) Appl. No.: 12/933,524

(22) PCT Filed: Mar. 31, 2009

(86) PCT No.: PCT/JP2009/056670
§ 371 (c)(1), (2), (4) Date: Sep. 20, 2010

(87) PCT Pub. No.: WO2009/123197
PCT Pub. Date: Oct. 8, 2009

(65) Prior Publication Data
US 2011/0021725 A1   Jan. 27, 2011

(30) Foreign Application Priority Data

Mar. 31, 2008 (JP) .................. 2008-089389
Mar. 31, 2008 (JP) .................. 2008-089425

(51) Int. Cl.
*C08F 2/04* (2006.01)
*C08F 20/06* (2006.01)
*B01J 19/24* (2006.01)
*C07C 57/07* (2006.01)

(52) U.S. Cl.
USPC ............... 526/75; 526/77; 526/88; 526/920; 526/930; 422/131; 422/622

(58) Field of Classification Search .............. 526/75, 526/88, 920, 930, 77; 422/131, 622; 562/598
See application file for complete search history.

(56) References Cited

U.S. PATENT DOCUMENTS 5,210,298 A   5/1993   Shimomura et al.
6,444,744 B1  9/2002   Fujimaru et al.
(Continued)

FOREIGN PATENT DOCUMENTS

WO   00/55245   9/2000
WO   03/051940  6/2003

*Primary Examiner* — Fred M Teskin
(74) *Attorney, Agent, or Firm* — Roylance, Abrams, Berdo & Goodman, L.L.P.

(57) ABSTRACT

An apparatus (2) includes a neutralization tank (3), a pump (4), a heat exchanger (6), a line mixer (8), a polymerizer (10), a first pipe (12), a second pipe (14), a third pipe (16), a fourth pipe (18), and a fifth pipe (20). Continuously supplied into the neutralization tank (3) are a monomer aqueous solution and a basic aqueous solution, so as to prepare a mixture solution. The mixture solution is circulated through the first pipe (12), the pump (4), the second pipe (14), the heat exchanger (6), and the third pipe (16). The mixture solution is supplied to the polymerizer through the fourth pipe (18). The apparatus (2) satisfies a requirement that a value X is not more than 200, which value X is found according to the following expression: "$X=(V/F) \cdot A$", wherein V is a volume of the mixture solution present in a neutralization system, F is a flow volume of the mixture solution to be supplied to a polymerization system, and A is a contact area of the mixture solution present in the neutralization system with a device(s) and a pipe(s) constituting the neutralization system. With this arrangement, it is possible to provide a water absorbent resin having superior whiteness.

21 Claims, 2 Drawing Sheets

U.S. PATENT DOCUMENTS

| | | | |
|---|---|---|---|
| 7,183,427 B2 * | 2/2007 | Wakita | 562/115 |
| 2008/0194863 A1 | 8/2008 | Weismantel et al. | |
| 2008/0242816 A1 | 10/2008 | Weismantel et al. | |
| 2009/0221746 A1 | 9/2009 | de Marco et al. | |

* cited by examiner

PRODUCTION METHOD AND PRODUCTION APPARATUS OF PARTICULATE WATER ABSORBING AGENT CONTAINING WATER ABSORBENT RESIN AS MAIN COMPONENT

TECHNICAL FIELD

The present invention relates to a production method and a production apparatus of a particulate water absorbing agent containing a water absorbent resin as a main component. More specifically, the present invention relates to how to improve neutralization of an acid group-containing monomer in a case where the water absorbent resin is produced from the acid group-containing monomer.

BACKGROUND ART

In recent years, a water absorbent resin is widely used as a constituent material, i.e., a water absorbing agent of sanitary materials, such as disposable diapers, sanitary napkins, and incontinent pads, for the purpose of absorbing body fluids. Well-known examples of the water absorbent resin are as follows: crosslinked partially neutralized polyacrylic acid; a hydrolyzed starch-acrylic acid graft polymer; a saponified vinyl acetate-acrylic ester copolymer; a hydrolyzed acrylonitrile copolymer or a crosslinked acrylonitrile copolymer; a hydrolyzed acrylamide copolymer or a crosslinked acrylamide copolymer; and a crosslinked cationic monomer. Among them, the crosslinked partially neutralized polyacrylic acid is especially preferably used in view of its properties and cost.

The crosslinked partially neutralized polyacrylic acid can be prepared by polymerizing a monomer component containing acrylic acid salt (acrylate). The acrylic acid salt can be prepared by a neutralization reaction of acrylic acid and a basic material. The neutralization is performed by mixing the acrylic acid and the basic material in a neutralization tank. The neutralization may be performed by mixing the acrylic acid and the basic material by use of a line mixer. The neutralization reaction generates neutralization heat. An acrylic acid aqueous solution in the neutralization tank is circulated through a heat exchanger so that a temperature of the acrylic acid aqueous solution can be adjusted. The aqueous solution is continuously supplied to a polymerization system through a pipe. Finally, in the polymerization system, the acrylic acid (salt) causes a polymerization reaction. Such a neutralization step is disclosed in U.S. Pat. No. 5,210,298, U.S. Patent Application Publication No. 2008/242816, International Publication No. WO 2007/028747 pamphlet, and U.S. Patent Application Publication No. 2008/194863.

In some sanitary products, the particulate water absorbing agent is used in such a manner that the particulate water absorbing agent is combined with white pulp. In view of this, the use of a particulate water absorbing agent having excellent whiteness for a sanitary product gives a user less uncomfortable feeling when he/she uses it. From the viewpoint, the particulate water absorbing agent is required to be white. In other words, it is necessary to prevent the particulate water absorbing agent from being colored.

In order to achieve the improvement of whiteness and the prevention of coloring of the particulate water absorbent resin, various water absorbent resins and techniques were proposed as follows: a water absorbent resin having excellent whiteness, which is produced from a monomer component containing acrylic acid (salt) and a given amount of methoxyphenol (International Publication No. WO 2003/051940 pamphlet); a technique for preventing coloring of a water absorbent resin by controlling hydroquinone in acrylic acid to be 0.2 wt ppm or less (U.S. Pat. No. 6,444,744); and a technique for preventing coloring of a water absorbent resin by adding a reducing agent (International Publication No. WO 2000/55245 pamphlet).

However, particulate water absorbing agents prepared by continuous polymerization often have different degrees of whiteness. Since demand for the whiteness of the particulate water absorbing agent is high, there is still room for improving the whiteness of the particulate water absorbing agent. Further, there have been used techniques for preventing coloring, such as: a technique in which a degree of purity of a raw material of the particulate water absorbing agent, such as acrylic acid, is highly increased; a technique in which polymerization conditions and/or drying conditions for preparing a water absorbent resin are set moderate; and a technique in which a new color protection agent (for example, a reducing agent) is used. However, such conventional techniques may cause an increase in production cost, a decrease in productivity, a decrease in security due to the use of the color protection agent, a decrease in water-absorbing property, and the like problems.

Further, some troubles may cause the polymerization system to stop working. Moreover, the polymerization system is purposely caused to stop working in some cases. When the polymerization system stops its operation, an aqueous solution remains within a pipe connecting the neutralization system and the polymerization system. The aqueous solution thus remaining in the pipe causes a polymerization reaction of the monomer component therein. Due to the polymerization reaction, gel is generated and adhered to an internal surface of the pipe. In order to remove the gel, it is necessary to dispose of the aqueous solution remaining in the pipe and wash the pipe before the polymerization system is restarted. This washing takes a lot of times and troubles. That is, the disposal of the aqueous solution and the washing of the pipe decrease the productivity of the water absorbent resin.

Citation List
Patent Literature 1
U.S. Pat. No. 5,210,298
Patent Literature 2
U.S. Patent Application Publication No. 2008/242816
Patent Literature 3
International Publication No. WO 2007/28747 pamphlet
Patent Literature 4
U.S. Patent Application Publication No. 2008/194863
Patent Literature 5
International Publication No. WO 2003/051940 pamphlet
Patent Literature 6
U.S. Pat. No. 6,444,744
Patent Literature 7
International Publication No. WO 2000/55245 pamphlet

SUMMARY OF INVENTION

The present invention is accomplished in view of the above problems. An object of the present invention is to provide a particulate water absorbing agent excellent in whiteness. Further, another object of the present invention is to improve the productivity of the particulate water absorbing agent.

Inventors of the present invention diligently studied on how to restrain a difference in whiteness between produced particulate water absorbing agents. As a result of the diligent study, the inventors of the present invention found that a neutralization step contributes to the difference in whiteness between the produced particulate water absorbing agents. In order to solve the problem, the inventors also found that by setting the after-mentioned value X within a given range, it is possible to stably produce a particulate water absorbing agent having excellent whiteness.

That is, a method of the present invention for producing a particulate water absorbing agent includes the steps of: (a) circulating, in a neutralization system including a neutralization tank, a mixture solution containing an acid group-containing monomer and salt obtained by a neutralization reaction of the acid-containing monomer with a basic material; (b) continuously supplying, to a polymerization system, a part of the mixture solution that is being circulated; and (c) polymerizing a monomer component of the mixture solution in the polymerization system, and the method satisfies a requirement that a value X is not more than 200, the value X being found according to the following expression:

$$X=(V/F) \cdot A$$

wherein V (kg) is a volume of the mixture solution present in the neutralization system, F (kg/h) is a flow volume of the mixture solution to be supplied to the polymerization system, and A($m^2$) is a contact area of the mixture solution present in the neutralization system with a device(s) and a pipe(s) constituting the neutralization system, It is preferable that a residence time (V/F) of the mixture solution in the neutralization system be not more than 10 hours. Further, it is preferable that the flow volume F be not less than 100 kg/h. Furthermore, it is preferable that the mixture solution in the neutralization tank have a monomer concentration of 30 to 70 mass %.

It is preferable that the method of the present invention further include, between the steps (b) and (c), the step of: (d) adding the basic material to the mixture solution so as to increase a neutralization ratio of the mixture solution. Further, it is preferable that the mixture solution have a neutralization ratio of 30 to 90 mol % right after the step (d).

Moreover, it is preferable that the mixture solution in the neutralization system be circulated through the neutralization tank and a loop-shaped closed flow channel (loop) attached to the neutralization tank.

In the method of the present invention, the neutralization system may include the neutralization tank, a first loop, and a second loop. In the method, the mixture solution in the neutralization tank is circulated through the first loop; the mixture solution is drawn from the neutralization tank or the first loop into the second loop so that the mixture solution is carried through the second loop to a place closer to the polymerization system than to the first loop; and the mixture solution then returns back through the second loop to the neutralization tank or the first loop.

Another method of the present invention for producing a water absorbent resin, includes the steps of: (1) in a neutralization system including a neutralization tank, a first loop, and a second loop, circulating through the first loop a mixture solution which is present in the neutralization tank and which contains an acid group-containing monomer and salt obtained by a neutralization reaction of the acid group-containing monomer with a basic material; (2) causing the mixture solution to be drawn from the neutralization tank or the first loop into the second loop so that the mixture solution is carried through the second loop to a place closer to a polymerization system than to the first loop, and then causing the mixture solution to return back through the second loop to the neutralization tank or the first loop; and (3) continuously supplying the mixture solution from the neutralization system to the polymerization system.

In the present invention, the monomer is preferably acrylic acid. Further, it is preferable that the acrylic acid contain a polymerization inhibitor by 1 ppm to 200 ppm. Moreover, it is preferable that the acrylic acid be purified by crystallization or distillation, and the acrylic acid be then supplied to the neutralization system within 96 hours after the purification. It is preferable that the neutralization system be connected to a production facility of the acrylic acid via a pipe.

It is preferable that the polymerization system carry out continuous kneader polymerization or continuous belt polymerization.

A production apparatus of the present invention for producing a water absorbent resin includes a neutralization system; a polymerization system; and a pipe connecting the neutralization system to the polymerization system. The neutralization system includes a neutralization tank in which to store a mixture solution containing an acid group-containing monomer and salt obtained by a neutralization reaction of the acid group-containing monomer with a basic material; a first loop for drawing the mixture solution from the neutralization tank and for returning the mixture solution back to the neutralization tank; and a second loop for drawing the mixture solution from the neutralization tank or the first loop so that the mixture solution is carried through the second loop to a place closer to the polymerization system than to the first loop, and for returning the mixture solution back to the neutralization tank or the first loop. In the production apparatus, the mixture solution is continuously supplied from the neutralization system to the polymerization system via the pipe, and the production apparatus satisfies a requirement that a value X is not more than 200, the value X being found according to the following expression:

$$X=(V/F) \cdot A$$

wherein V (kg) is a volume of the mixture solution present in the neutralization system, F (kg/h) is a flow volume of the mixture solution to be supplied to the polymerization system, and A($m^2$) is a contact area of the mixture solution present in the neutralization system with a device(s) and a pipe(s) constituting the neutralization system.

Further, in the production apparatus of the present invention, it is preferable that the acid group-containing monomer and a mixture solution of the basic material and water are continuously supplied to the first loop.

Further, in the production apparatus of the present invention, it is preferable that a headspace in the neutralization tank have a volume of 50% to 90% with respect to a volume of the neutralization tank; and the headspace be sealed with mixed gas of oxygen and inactive gas in which mixed gas an oxygen concentration is adjusted in advance.

Moreover, in the production apparatus of the present invention, it is preferable that the neutralization system further include a pipe that is connected to a production facility of the acid group-containing monomer.

Additional objects, features, and strengths of the present invention will be made clear by the description below. Further, the advantages of the present invention will be evident from the following explanation in reference to the drawings.

REFERENCE SIGNS LIST

Figure 1:
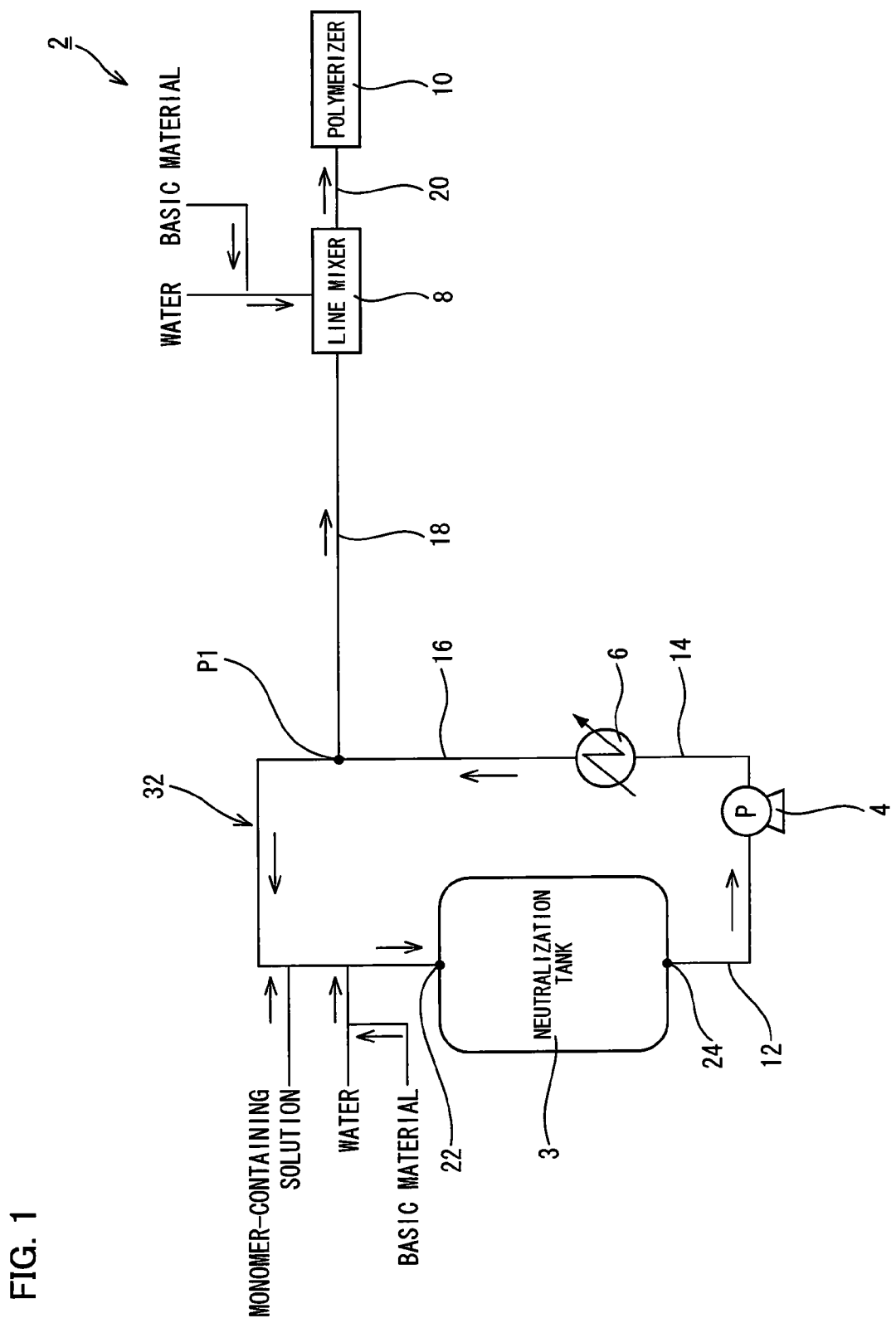
FIG. 1 is a conceptual diagram illustrating an apparatus for use in a production method according to one embodiment of the present invention.

| 2, 26 | Apparatus |
|---|---|
| 3 | Neutralization Tank |
| 4 | Pump |
| 6 | Heat Exchanger |
| 8 | Line Mixer |
| 10 | Polymerizer |
| 12 | First Pipe |
| 14 | Second Pipe |
| 16 | Third Pipe |
| 18 | Fourth Pipe |
| 20 | Fifth Pipe |
| 30 | Sixth Pipe |
| 22 | Inlet |
| 24 | Outlet |
| 32 | First Loop |
| 34 | Second Loop |

DESCRIPTION OF EMBODIMENTS

The following describes details of a production method according to the present invention for producing a particulate water absorbing agent containing a water absorbent resin as a main component, but the scope of the present invention is not limited to the following description. Further, the present invention is not limited to the following examples, but may be appropriately modified within the gist of the present invention.

(1) DEFINITION OF TERMS (a) "Water Absorbent Resin"

The "water absorbent resin" in the specification of the present invention is a water-swelling and water-insoluble polymer gelatinizer, i.e., a polymer gelatinizer having properties as follows: a centrifuge retention capacity (CRC, defined by ERT441.2-02 (2002)) is essentially 5 g/g or more, more preferably 10 g/g to 100 g/g, further preferably 20 g/g to 80 g/g; and a water-soluble content (Extractables, defined by ERT470.2-02 (2002)) in the resin is essentially 0 wt % to 50 wt %, more preferably 0 wt % to 30 wt %, further preferably 0 wt % to 20 wt %, especially preferably 0 wt % to 10 wt %. The water absorbent resin is not limited to a resin fully constituted by a polymer (a ratio of the polymer contained in the resin is 100%), but may contain an additive etc. (described later) within a range that can maintain the aforementioned properties.

(b) "Polyacrylic Acid (Salt)"

The "polyacrylic acid (salt)" in the specification of the present invention is a polymer mainly containing acrylic acid (salt) as a repeating unit. More specifically, the polyacrylic acid (salt) is a polymer containing, as a monomer exclusive of a crosslinking agent, acrylic acid (salt) by essentially 50 mol % to 100 mol %, more preferably 70 mol % to 100 mol %, and further preferably 90 mol % to 100 mol %. It is especially preferable that the polyacrylic acid (salt) be a polymer containing acrylic acid (salt) by substantially 100 mol %. The salt as a polymer essentially contains a water-soluble salt, and is more preferably monovalent salt, further preferably alkali metal salt or ammonium salt. Among them, the alkali metal salt is preferable, and sodium salt is especially preferable.

(c) "Water Absorbing Agent"

The "water absorbing agent" in the specification of the present invention is a gelatinizer for gelatinizing aqueous liquid, which gelatinizer contains the water absorbent resin as a main component. Particularly, the water absorbing agent having a particle shape is referred to as a "particulate water absorbing agent". The aqueous liquid is not limited to water, but may be urine, blood, feces, waste fluid, moisture, vapor, ice, a mixture of water and organic solvent and/or inorganic solvent, rain water, ground water, and the like, as long as the aqueous liquid includes water. Among them, the aqueous liquid is preferably urine, particularly preferably human urine.

An amount of the water absorbent resin (the polyacrylic acid (salt) water absorbent resin) included in the particulate water absorbing agent preferably ranges from 70 wt % to 99.9 wt %, more preferably from 80 wt % to 99.7 wt %, still more preferably from 90 wt % to 99.5 wt %, with respect to an entire amount of the particulate water absorbing agent. As other components except for the water absorbent resin, water is preferably contained from the viewpoint of water-absorbing speed and resistance of powder (particles) to impact. Further, the after-mentioned additives may be used as required.

(d) "EDANA" and "ERT"

The "EDANA" is an abbreviation for European Disposables and Nonwovens Association. The "ERT" is an abbreviation for a measuring method for a water absorbent resin, called "EDANA Recommended Test Methods", which is European standard (almost world standard). In the specification of the present invention, the properties of the water absorbent resin are measured by referring to the ERT original text (publicly known document, revised in 2002), if not otherwise specified.

(e) "Particle"

The "particle" in the specification of the present invention is a solid whose particle diameter defined by sieve classification is not more than 5 mm and which has fluidity. A moisture content of the particle is not especially limited as long as the particle is a solid, but normally is less than 30 wt %, more preferably 20 wt % or less. Further, a lower limit of the particle diameter is, for example, 1 nm. Further, the particle is not especially limited as long as it has a given fluidity as powder, and may be, for example, a solid whose Flow Rate (defined by ERT450.2-02 (2002)) can be measured, or a solid which can be classified by sieve (defined by ERT420.2-02 (2002)). A shape of the solid is not especially limited, and the solid may be a particle having an irregularly-pulverized shape, a spherical shape, or a substantially spherical shape, or a granulated particle (agglomerated particle) having these shapes. It is preferable that the solid contain the particle having an irregularly-pulverized shape.

In the specification of the present invention, a range "from X to Y" means a range of not less than X but not more than Y. Further, "ton (t)", which is a unit of weight, means "metric ton".

(2) PRODUCTION METHOD OF PARTICULATE WATER ABSORBING AGENT

Initially, with reference to drawings, the following describes a production method of the present invention for producing a particulate water absorbing agent containing a water absorbent resin as a main component.

Figure 2:
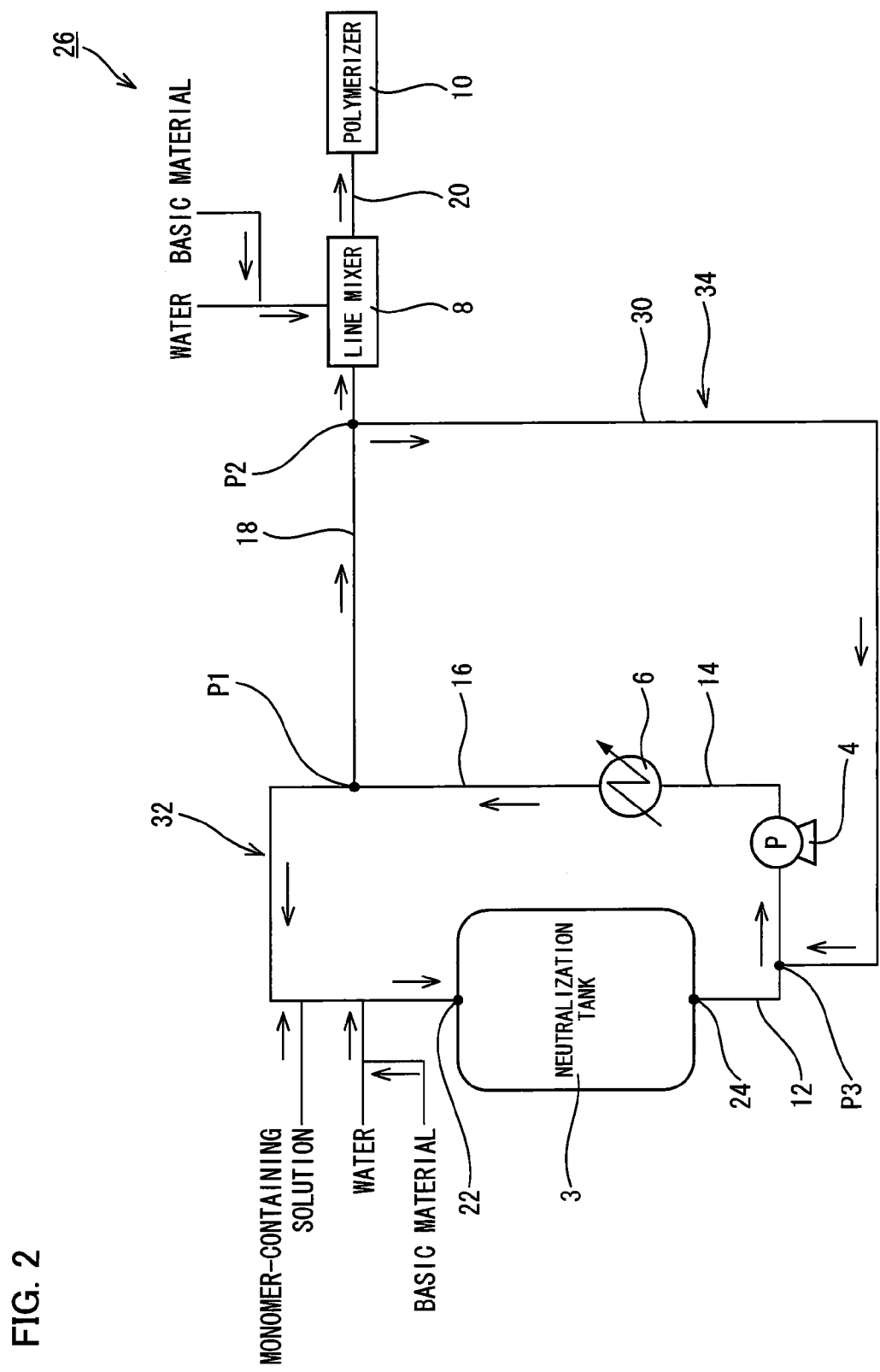
FIG. 2 is a conceptual diagram illustrating an apparatus for use in a production method according to another embodiment of the present invention.

FIG. 1 is a conceptual diagram illustrating an apparatus 2 for use in a production method of the present invention for producing a particulate water absorbing agent. FIG. 2 is a conceptual diagram illustrating an apparatus 26 for use in another production method of the present invention for producing a particulate water absorbing agent. These apparatuses 2 and 26 are just exemplary embodiments of the present invention, and the technical scope of the present invention is not limited to the apparatuses illustrated in FIG. 1 and FIG. 2.

The apparatus 2 illustrated in FIG. 2 includes a neutralization tank 3, a pump 4, a heat exchanger 6, a line mixer 8, a polymerizer 10, a first pipe 12, a second pipe 14, a third pipe 16, a fourth pipe 18, and a fifth pipe 20. The apparatus 26 illustrated in FIG. 2 includes a sixth pipe 30 in addition to the members included in the apparatus 2 of FIG. 1.

In FIG. 1 and FIG. 2, the neutralization tank 3 includes an inlet 22 and an outlet 24. The first pipe 12 connects the outlet 24 to the pump 4. The second pipe 14 connects the pump 4 to the heat exchanger 6. The third pipe 16 connects the heat exchanger 6 to the inlet 22. The fourth pipe 18 connects a certain point P1 on the third pipe 16 to the line mixer 8. The fifth pipe 20 connects the line mixer 8 to the polymerizer 10.

Further, in FIG. 2, the sixth pipe 30 connects a certain point P2 on the fourth pipe 18 to a certain point P3 on the first pipe 12.

In FIG. 1 and FIG. 2, the first pipe 12, the second pipe 14, and the third pipe 16 form a closed flow channel (hereinafter, also referred to as "first loop 32").

Further, in FIG. 2, a part of the first pipe 12, the second pipe 14, a part of the third pipe 16, a part of the fourth pipe 18, and the sixth pipe 30 form a closed flow channel (hereinafter, also referred to as "second loop 34"). The first loop 32 and the second loop 34 are also referred to as a circulation loop.

In the present invention, the "closed flow channel" is a pipe system in which an origin and an end of a flow of liquid coincide with each other. As long as the origin and the end coincide with each other, the pipe system may include a tank, a heat exchanger, a pump, and the like device between the origin and the end. Further, the closed flow channel may be a closed flow channel having a curved shape (narrowly-defined loop), or may be a closed flow channel having a polygonal shape formed by a plurality of linear pipes. The closed flow channel may be arranged in a three-dimensional form.

In the present invention, a device group including the neutralization tank 3, the pump 4, the heat exchanger 6, and the first loop 32 (and the second loop 34 in the case of FIG. 2) is referred to a "neutralization system". In the neutralization system, a mixture solution is circulated. Details of the mixture solution will be explained later. Further, the concept of "circulation" in the present invention includes not only circulating of the mixture solution in the closed flow channel, but also stirring of the mixture solution by a stirring blade provided in the neutralization tank 3.

Further, in the present invention, a device group including the line mixer 8, the fifth pipe 20, and the polymerizer 10 is referred to as a "polymerization system". In the polymerization system, a monomer component included in a mixture solution, which will be explained later, is polymerized, whereby a polymer gel is prepared. Further, the polymerization system includes a device, a pipe, and the like for adding to the mixture solution a polymerization initiator, an internal crosslinking agent, a basic material, and the like. Moreover, the polymerization system may include several devices, pipes, and the like. Specifically, the polymerization system may include at least two polymerizers.

In the production method of the present invention for producing a particulate water absorbing agent, a monomer-containing solution and a basic aqueous solution are continuously supplied to the neutralization system. The monomer-containing solution essentially includes an acid-group-containing monomer. The basic aqueous solution is an aqueous solution prepared by mixing a basic material and water.

In the apparatuses 2 and 26 of the present invention, the monomer-containing solution and the basic aqueous solution are continuously supplied to the third pipe 16 through which the monomer-containing solution and the basic aqueous solution are supplied to the neutralization tank 3. As such, the monomer-containing solution and the basic aqueous solution are supplied to the neutralization tank 3 not directly but via the third pipe 16. This arrangement is preferable because efficiency of mixing these solutions increases. However, even with such an arrangement in which the monomer-containing solution and the basic aqueous solution are directly supplied to the neutralization tank 3, it is possible to obtain the effect of the present invention.

In this way, it is possible to prepare a mixture solution containing salt obtained by a neutralization reaction between the monomer component and the basic material. The mixture solution is circulated through the first loop 32 (and the second loop 34 in the case of FIG. 2) by the pump 4. At this time, neutralization heat is generated due to the neutralization reaction between the monomer component and the basic material. However, the heat exchanger 6 provided on the first loop 32 carries out cooling or heating on the mixture solution, thereby making it possible to adjust and maintain a temperature of the mixture solution within a desired range. This achieves a given neutralization ratio.

In the present invention, a part of the mixture solution circulating in the neutralization system is continuously supplied to the polymerization system. In the polymerization system, the basic material may be continuously supplied to the mixture solution if needed, in order to further increase the neutralization ratio of the mixture solution. In this case, it is preferable to mix the mixture solution with the basic material in the line mixer 8, from the viewpoint of the mixing efficiency. Further, the internal crosslinking agent, the polymerization initiator, and the like may be added to the mixture solution. In this case, from the viewpoint of the mixing efficiency, it is preferable to add the internal crosslinking agent, the polymerization initiator, and the like to the mixture solution at the line mixer 8 or at its upstream or downstream portion (not shown).

The continuous supply of the mixture solution to the polymerizer 10 causes a polymerization reaction, thereby generating a polymer gel. The polymer gel is then subjected to the after-mentioned processes, thereby preparing a particulate water absorbing agent.

In the present invention, the circulation of the mixture solution in the neutralization system, the supply of the mixture solution to the polymerization system, and the polymerization of the mixture solution are carried out at the same time.

A material of the devices, the pipes, and the like in the apparatuses 2 and 26 of the present invention is not especially limited, but stainless steel that is generally used can be used as the material. Furthermore, a steel pipe whose internal surface is coated with fluorine resin, a pipe made of fluorine resin, or the like pipe may be also used.

In the present invention, a relationship between a residence time during which the mixture solution is retained in the neutralization system and a contact area of the mixture solution to the devices, pipes, and the like constituting the neutralization system is defined. That is, the production method of the present invention satisfies a requirement that a value X defined by the following expression (1) is not more than 200.

$$X=(V/F)\cdot A \quad (1)$$

In the expression (1), V (kg) is a volume of the mixture solution present in the neutralization system; F (kg/h) is a flow volume of the mixture solution to be supplied to the polymerization system; and A ($m^2$) is a contact area of the mixture solution present in the neutralization system with the devices and the pipes constituting the neutralization system. Therefore, V/F (h) is the residence time of the mixture solution in the neutralization system.

The "volume (V) of the mixture solution present in the neutralization system" indicates a total volume of the mixture solution present in the neutralization tank 3, the pump 4, the heat exchanger 6, and the first loop 32 (and the second loop 34 in the case of FIG. 2). That is, when Va is a volume of the mixture solution present in the neutralization tank 3, Vb is a volume of the mixture solution present in the pump 4, Vc is a volume of the mixture solution present in the heat exchanger 6, and Vd is a volume of the mixture solution present in the pipes constituting the circulation loop, a total sum of Va, Vb, Vc, and Vd equals to the volume of the mixture solution present in the neutralization system. That is, the mixture solution present in devices, pipes, and the like not included in the circulation loop is not included in the mixture solution present in the neutralization system. On the other hand, in a case where the circulation loop further includes an additional device, pipe, or the like that is not shown in FIG. 1 and FIG. 2), the mixture solution present in the additional device, pipe, or the like is also taken as the mixture solution present in the neutralization system. The "volume of the mixture solution present in the neutralization system" is not especially limited, but is preferably in a range from 100 kg to 30000 kg, more preferably 200 kg to 10000 kg.

The volume of the mixture solution present in the neutralization system is constant in a steady state because a total volume of the mixture solution to be supplied to the neutralization system is generally equal to a total volume of the mixture solution to be supplied to the polymerization system. However, in some cases, the supply volume to the neutralization system and the supply volume to the polymerization system may become off balance, with the result that the volume of the mixture solution present in the neutralization system may be changed. In this case, it is also possible to find the value X by use of an arithmetic average of measurement values of the volume of the mixture solution, which are measured at given time intervals (of 1 hour, for example).

The "flow volume (F) of the mixture solution to be supplied to the polymerization system" is measured by a flowmeter provided in a pipe that connects the neutralization system and the polymerization system. The pipe that connects the neutralization system and the polymerization system indicates more specifically the fourth pipe 18 in the case of the apparatus 2, and a pipe located between the point P2 and the line mixer 8 in the case of the apparatus 26. Normally, the flow volume can be found by dividing, by operation hours, the total volume of the mixture solution to be supplied to the polymerization system. The flow volume is not especially limited, but is preferably in a range from 30 kg/h to 30000 kg/h, more preferably 100 kg/h to 10000 kg/h.

The "contact area (A) of the mixture solution present in the neutralization system with the devices and the pipes constituting the neutralization system" is a contact area of the mixture solution in which area the mixture solution has contact with internal surfaces of all constituent members in the neutralization system, such as the tank, the devices, and the pipes. That is, when Aa is a contact area of the mixture solution present in the neutralization tank 3 with an internal surface of the neutralization tank 3, Ab is a contact area of the mixture solution present in the pump 4 with an internal surface of the pump 4, Ac is a contact area of the mixture solution present in the heat exchanger 6 with an internal surface of the heat exchanger 6, and Ad is a contact area of the mixture solution present in the pipes constituting the circulation loop with internal surfaces of these pipes, a total sum of Aa, Ab, Ac, and Ad equals to the contact area of the mixture solution present in the neutralization system with the devices and the pipes constituting the neutralization system. That is, the contact area A does not include a contact area of the mixture solution present in a device(s) or a pipe(s) not included in the circulation loop with an internal surface(s) of the device(s) or the pipe(s). In a case where the circulation loop further includes a device or a pipe that is not shown in the figure, a contact area of the mixture solution present in the device or the pipe with an internal surface of the device of the pipe is also taken as the contact area A.

Further, in the present invention, it is not necessary that all of the tank, devices, pipes, and the like be filled with the mixture solution, and there may exist a headspace. In this case, the contact area indicates an area of a part of the tank, devices, pipes, and the like which area actually has contact with the mixture solution, and does not includes an area of the headspace.

The headspace is not limited in any particular manner, but the neutralization tank 3, for example, may include a headspace having a volume of 50 vol % to 90 vol % with respect to the volume of the neutralization tank 3. Further, in this case, from the viewpoint of preventing the mixture solution to be polymerized, it is preferable that the headspace be sealed with mixed gas of oxygen and/or inactive gas in which mixed gas an oxygen concentration is adjusted in advance.

The contact area of the mixture solution present in the neutralization system with the devices and the pipes constituting the neutralization system is constant in a steady state, because the total volume of the mixture solution to be supplied to the neutralization system generally equals to the total volume of the mixture solution to be supplied to the mixture polymerization system. However, in some cases, the supply volume to the neutralization system and the supply volume to the polymerization system may be off balance, with the result that the volume of the mixture solution present in the neutralization system may be changed. In this case, it is also possible to find the value X by calculating an average contact area by use of an arithmetic average of measurement values of the volume of the mixture solution, measured at given time intervals (of 1 hour, for example).

In the present invention, the value X found according to the expression (1) is controlled within a range from 0.5 to 200, preferably from 1 to 70, more preferably 10 to 65, still further preferably 20 to 62. This makes it possible to prepare a particulate water absorbing agent having excellent whiteness.

The points P1, P2, and P3 can be located in any positions and are not especially limited, provided that the points P1, P2, and P3 are located on the third pipe 16, the fourth pipe 18, and the first pipe 12, respectively. However, the point P2 is preferably located as close to the polymerization system as possible, because of the following reason.

That is, in a case where the polymerization system stops its operation due to some trouble or maintenance of the apparatus, the supply of the mixture solution to the polymerization system is also stopped. At this time, the mixture solution remains in a pipe connecting the neutralization system to the polymerization system. This causes deterioration of the mixture solution due to a chemical reaction or the like. From the viewpoint of the quality of the particulate water absorbing agent, the present mixture solution is discarded.

On the other hand, the mixture solution in the circulation loop sometimes continues circulating regardless of whether the polymerization system works or not. In view of this, when the point P2 is located as close to the polymerization system as possible, it is possible to reduce a volume of the mixture solution to be discarded and a length of a pipe to be washed, thereby making it possible to increase the productivity of the particulate water absorbing agent.

In a production plant for the particulate water absorbing agent, the neutralization system is placed away from the polymerization system for the reason of layout. The above arrangement is significantly effective in such a case. Further, in the above arrangement, the mixture solution in the circulation loop can be maintained at appropriate temperatures, thereby yielding a significant effect when the polymerization system restarts.

That is, in the apparatus 26 including two circulation loops, the mixture solution in the neutralization tank 3 is circulated through the first loop 3; the mixture solution is then drawn into the second loop 34 from the neutralization tank 3 or the first loop 32 so that the mixture solution is carried to a position closer to the polymerization system than to the first loop 32; and finally the mixture solution is returned back to the neutralization tank 3 or the first loop 32.

When a length Lb is defined from the point P1 to the point P2 on the fourth pipe 18 in the apparatus 26 and a length La is defined from the point P2 to the line mixer 8 on the fourth pipe 18 in the apparatus 26, the length La is preferably not more than 20 m, more preferably not more than 10 m. Further, a ratio of Lb to La (Lb/La) is preferably not less than 10, more preferably not less than 20, further preferably not less than 30. By setting the ratio (Lb/La) to fall within the range, the low cost and the high productivity can be achieved.

Further, in the apparatus 26, when a length Lc is defined as an entire length of the first loop 32 and a length Ld is defined as an entire length of the second loop 34, a ratio of Ld to Lc (Ld/Lc) is preferably not less than 10, more preferably not less than 20, further preferably not less than 30. By setting the ratio (Ld/Lc) to fall within the range, the low cost and the high productivity can be achieved.

In the present invention, the particulate water absorbing agent containing a water absorbent resin as a main component can be obtained in accordance with the following steps. That is, the water absorbent resin can be produced through a neutralization step, a polymerization step, a drying step, a crushing step, and a classification step. Subsequently, the particulate water absorbing agent can be produced through a surface crosslinking step, a cooling step, an additive addition step, and the like steps. The following describe these steps.

[Neutralization Step]

The neutralization step in the present invention is carried out in the neutralization system shown in FIG. 1 or FIG. 2. Into the neutralization system, the aforementioned monomer-containing solution and basic aqueous solution are continuously supplied.

The monomer-containing solution essentially contains an acid group-containing monomer. The acid group-containing monomer is not especially limited, but may be, for example, (meth)acrylic acid, maleic acid (anhydride), itaconic acid, cinnamic acid, vinyl sulfonic acid, allyl toluenesulfonic acid, vinyl toluenesulfonic acid, styrenesulfonic acid, 2-(meth)acrylamide-2-methylpropanesulfonic acid, 2-(meth)acryloylethanesulfonic acid, 2-(meth)acryloylpropanesulfonic acid, or the like. The monomer-containing solution may contain a monomer having no acid group, as well as the acid group-containing monomer. The monomer having no acid group is not especially limited, but may be, for example, a mercapto group-containing unsaturated monomer; a phenolic hydroxyl group-containing unsaturated monomer; an amide group-containing unsaturated monomer such as (meth)acrylamide, N-ethyl(meth)acrylamide, or N,N-dimethyl(meth)acrylamide; or an amino group-containing unsaturated monomer such as N,N-dimethylaminoethyl(meth)acrylate, N,N-dimethylaminopropyl(meth)acrylate, N,N-dimethylaminopropyl(meth)acrylamide. The monomer-containing solution may include a chelating agent, water, an organic solvent, and the like. Among them, from the viewpoint that a high-quality particulate water absorbing agent can be prepared at low cost, the acrylic acid is most preferably used as the acid group-containing monomer.

Further, the monomer-containing solution is preferably an aqueous solution irrespective of a condition of the monomer (i.e., whether the monomer is solid or liquid at a room temperature). This is because the aqueous solution can be easily handled. In the present invention, the "room temperature" ranges from 20° C. to 30° C.

That is, the monomer-containing solution is preferably a 10 wt % to 99 wt % monomer aqueous solution, more preferably 50 wt % to 100 wt % acrylic acid aqueous solution. Further, the monomer-containing solution is preferably at 0° C. to 50° C., more preferably at 25° C. to 50° C.

In a case where the monomer-containing solution contains other monomer(s) together with the acrylic acid, it is preferable that the monomer-containing solution contain the acrylic acid as a main component. In this case, a content of the acrylic acid with respect to a total amount of monomers is preferably not less than 50 mol %, more preferably not less than 80 mol %, further preferably not less than 95 mol % (the upper limit is 100 mol %).

The monomer-containing solution normally contains a polymerization inhibitor. The polymerization inhibitor is preferably a phenolic compound. Examples of the phenolic compound are alkylphenols and alkoxyphenols. The phenolic compound may have a substitutional group, which is preferably a t-butyl group, a methyl group, or an ethyl group, for example. A typical polymerization inhibitor is p-methoxyphenol. With respect to the monomer component, an amount of the polymerization inhibitor to be used ranges preferably from 1 wt ppm to 200 wt ppm, more preferably from 2 wt ppm to 180 wt ppm, further preferably from 10 wt ppm to 160 wt ppm, still further preferably from 20 wt ppm to 100 wt ppm. When the amount of the polymerization inhibitor falls within the range, it is possible to prevent a low rate of the polymerization reaction and to restrain coloring of the particulate water absorbing agent.

In the present invention, in a case where the acid group-containing monomer is acrylic acid, it is preferable to supply to the neutralization system purified acrylic acid prepared through a crystallization process and/or a distillation process. From the viewpoint of decreasing an amount of a residual monomer in the particulate water absorbing agent and preventing coloring of the particulate water absorbing agent, it is preferable to supply to the neutralization system the purified acrylic acid within preferably 96 hours, more preferably 72 hours, still more preferably 48 hours, especially preferably 24 hours, most preferably 12 hours after the acrylic acid has been subjected to the crystallization process and/or the distillation process.

In the present invention, it is preferable that a production facility for the acid group-containing monomer and a facility for the neutralization system be located adjacent to each other in such a manner that they are directly connected with each other via a pipeline. A length of the pipeline is not especially limited, but preferably not more than 30 km, more preferably not more than 10 km, further preferably not more than 5 km. In the middle of the pipeline may be provided a storage tank for the acid group-containing monomer as needed. Conventionally, it takes a certain amount of time to store or transport the acid group-containing monomer in the production facility thereof. Therefore, it takes around a week or a few dozens of days after the acid group-containing monomer is produced, until the acid group-containing monomer is supplied to the neutralization system. This contributes to coloring of the particulate water absorbing agent. However, by arranging the pipeline as above, it is possible to supply the acid group-containing monomer to the neutralization system at short times and to prevent the coloring of the particulate water absorbing agent.

In a case where the acid group-containing monomer is acrylic acid, the acrylic acid is preferably maintained at low temperatures at the time when the acrylic acid is transported or stored through the pipeline. Specifically, the acrylic acid is preferably at temperatures of not more than 30° C., more preferably at temperatures from a melting point of the acrylic acid to 25° C.

Further, the basic aqueous solution is not especially limited, provided that the basic aqueous solution initiates a neutralization reaction with the monomer to produce salt (for example, salt of sodium, lithium, potassium, ammonium, or an amine). However, from the viewpoint of properties and costs for the resultant particulate water absorbing agent, the basic aqueous solution is preferably a solution that produces sodium salt, more specifically, a sodium hydroxide aqueous solution.

Further, the basic aqueous solution is preferably an aqueous solution irrespective of a condition of the basic material (i.e., whether the basic material is solid or liquid at a room temperature). This is because the aqueous solution can be easily handled. A concentration of the basic aqueous solution is preferably 5 wt % to 80 wt %, more preferably 10 wt % to 50 wt %. Furthermore, the basic aqueous solution is maintained preferably at temperatures from 0° C. to 50° C., more preferably 25° C. to 50° C.

In the present invention, it is not necessary that the acid group-containing monomer supplied to the neutralization system be wholly neutralized. Normally, a part of the acid group-containing monomer is not neutralized and remains as it is. That is, in the mixture solution in the neutralization system, there exist an unneutralized acid group-containing monomer and salt of the acid group-containing monomer. In the present invention, the unneutralized acid group-containing monomer and the salt produced due to the neutralization of the acid group-containing monomer are collectively called monomer component.

In the present invention, a neutralization ratio of the acid group-containing monomer preferably ranges from 10 mol % to 90 mol %, more preferably from 20 mol % to 80 mol %, still more preferably from 25 to 75 mol %. By controlling the neutralization ratio of the acid group-containing monomer to fall within the range, it is possible to reduce an amount of a residual monomer in an obtained particulate water absorbing agent and to realize a particulate water absorbing agent having excellent whiteness.

In the present invention, a concentration (hereinafter, also referred to as "monomer concentration") of a monomer component in the mixture solution present in the neutralization system is preferably 30 wt % to 70 wt %, more preferably 30 wt % to 65 wt %, still more preferably 45 wt % to 65 wt %. By controlling the monomer concentration to fall within the range, excellent productivity can be achieved, which contributes to improvement of the particulate water absorbing agent in whiteness.

In the present invention, a temperature of the mixture present in the neutralization system is preferably 20° C. to 60° C., more preferably 30° C. to 50° C. By controlling the temperature to fall within the range, it is possible to restrain a polymerization reaction and generation of impurities.

Further, in the present invention, the residence time (V/F) of the mixture solution present in the neutralization system is preferably 0.1 to 10 hours, more preferably 0.1 to 5 hours, still more preferably 0.1 to 2 hours, especially preferably 0.1 to 1.7 hours. By controlling the residence time to fall within the range, it is possible to produce a particulate water absorbing agent having high whiteness and to reduce an amount of a residual monomer in the particulate water absorbing agent.

In the present invention, a flow volume F of the mixture solution to be supplied to the polymerization system is preferably 30 kg/h to 30000 kg/h, more preferably 100 kg/h to 25000 kg/h, still more preferably 2000 kg/h to 20000 kg/h. By controlling the flow volume to fall within the range, it is possible to produce a particulate water absorbing agent having excellent whiteness and to achieve further excellent productivity.

Moreover, in the present invention, it is also possible to further carry out a neutralization process in the after-mentioned polymerization step. That is, into the mixture solution supplied to the polymerization system is further supplied a basic aqueous solution at the line mixer 8. This supply operation allows the neutralization ratio to be increased. However, the neutralization ratio of the acid group-containing monomer is preferably 30 mol % to 90 mol %. The neutralization process carried out in the polymerization system is referred to as "second-stage neutralization" in the present invention.

[Polymerization Step]

In the polymerization step in the present invention, the monomer component obtained in the neutralization system is polymerized so as to generate a polymer gel. How to carry out polymerization is not limited in any particular manner, and may be, for example, aqueous solution polymerization, reverse phase suspension polymerization, bulk polymerization, or precipitation polymerization. Among them, from the viewpoint that the polymerization reaction can be easily controlled and a high-quality particulate water absorbing agent can be produced, the aqueous solution polymerization and the reverse phase suspension polymerization are more preferable, the aqueous solution polymerization is still more preferable, and continuous aqueous solution polymerization is especially preferable. How to carry out the continuous aqueous solution polymerization is, for example: a method in which polymerization is carried out while hydrogel prepared in a uniaxial or multiaxial (preferably double-arm) kneader is being crushed (hereinafter referred to as "continuous kneader polymerization"); or a method in which a monomer aqueous solution is supplied to a given container or a driven belt so as to be polymerized (hereinafter referred to as "continuous belt polymerization"). Any of these polymerization methods and the neutralization system are successively carried out so that a high-property particulate water absorbing agent can be continuously produced with high productivity. Further, subsequent steps carried out after the polymerization step can be also connected to each other so that they are carried out successively as appropriate.

In the polymerization step, an internal crosslinking agent may be added to the mixture solution as needed. The addition of the internal crosslinking agent makes it possible to restrain that the particulate water absorbing agent dissolves when the particulate water absorbing agent absorbs body fluids such as urine or blood. The internal crosslinking agent is not especially limited, and may be, for example, compounds having at least 2 polymerizable unsaturated groups within one molecule or compounds having at least 2 reactive groups within one molecule. Among such compounds, the compound having at least 2 polymerizable unsaturated groups is preferable. Concrete examples of the internal crosslinking agent encompass, for example, N,N'-methylene bis(meth)acrylamide, (poly)ethylene glycol di(meth)acrylate, (poly)propylene glycol di(meth)acrylate, trimethylolpropane tri(meth)acrylate, glycerine tri(meth)acrylate, glycerineacrylatemethacrylate, ethylene oxide denatured trimethylolpropane tri(meth)acrylate, pentaerythritol hexa(meth)acrylate, triallyl cyanurate, triallyl isocyanurate, triallyl phosphate, triallyl amine, poly-allyloxyalcane, (poly)ethyleneglycol diglycidylether, glycerol diglycidylether, ethylene glycol, polyethylene glycol, propylene glycol, glycerin, 1,4-butanediol, pentaerythritol, ethylenediamine, ethylene carbonate, propylene carbonate, polyethyleneimine, glycidyl(meth)acrylate, and the like. These internal crosslinking agents can be used solely or at least two types of the internal crosslinking agents can be used in combination in consideration of reactivity.

An amount of the internal crosslinking agent to be used may be determined as appropriate depending on an intended property of the particulate water absorbing agent, but is preferably 0.001 mol % to 5 mol %, more preferably 0.01 mol % to 5 mol % with respect to the monomer component. When the amount of the internal crosslinking agent is at least 0.001 mol %, it is possible to restrain a water soluble component in the particulate water absorbing agent. Further, when the amount of the internal crosslinking agent is not more than 5 mol %, it is possible to produce a particulate water absorbing agent having excellent absorption capacities.

In the polymerization step, a foaming agent, a hydrophilic polymer, a surfactant, a chain transfer agent, or the like can be optionally added to the mixture solution if necessary. Examples of the foaming agent encompass (hydrogen) carbonate, carbon dioxide, an azo compound, an inactive organic solvent, and the like. Examples of the hydrophilic polymer encompass starch and cellulose, starch and a derivative of the cellulose, polyvinyl alcohol, polyacrylic acid (salt), crosslinked polyacrylic acid (salt), and the like. Examples of the chain transfer agent encompass hypophosphorous acid (salt) and the like. An amount of these additives to be used is determined appropriately within a range in which the effects of the present invention are not lost. More specifically, with respect to 100 parts by mass of the monomer component, it is preferable that the foaming agent be not more than 30 parts by mass, the hydrophilic polymer be not more than 30 parts by mass, and the chain transfer agent be not more than 1 part by weight.

During the polymerization step, a polymerization initiator may be added to the mixture solution. The radical activity of the polymerization initiator promotes polymerization of the monomer component. The polymerization initiator is not especially limited, and one type or at least two types of polymerization initiators may be selected from polymerization initiators normally used in polymerization of a water absorbent resin in accordance with a type of a monomer component to be polymerized, polymerization conditions, and the like. More specifically, a thermal decomposition initiator and/or a photodecomposition initiator are(is) used. The thermal decomposition initiator is not especially limited. Examples of the thermal decomposition initiator encompass; persulfates such as sodium persulfate, potassium persulfate, and ammonium persulfate; peroxides such as hydrogen peroxide, t-butylperoxide, and methyl ethyl ketone peroxide; azo compounds such as an azonitryl compound, an azoamidine compound, a circular azoamidine compound, an azoamide compound, an alkyl azo compound, 2,2'-azobis(2-amidino-propane)dihydrochloride, and 2,2'-azobis[2-(2-imidazoline-2-yl)propane]dihydrochloride. Further, the photodecomposition initiator is not especially limited. Examples of the photodecomposition initiator encompass benzoin derivatives, benzyl derivatives, acetophenone derivatives, benzophenone derivatives, azo compounds, and the like. Among these polymerization initiators, from the viewpoint of low cost and reducing of the residual monomer, the thermal decomposition initiator is preferably used, and the persulfates are especially preferably used. Further, at least two types of the polymerization initiators may be used in combination. Furthermore, the thermal decomposition initiator and the photodecomposition initiator can be used in combination.

In a case where a reducing agent is also used, it is possible to promote decomposition of the polymerization initiators. Therefore, the combination of the reducing agent and the polymerization initiators may be employed as a redox initiator. The reducing agent is not especially limited, but may be, for example: (bi)sulfurous acid (salt) such as sodium sulfite, acid sodium sulfite, or the like; L-ascorbic acid (salt); reducing metal (salt) such as ferrous salt; an amine; or the like.

An amount of the polymerization initiator to be used in the polymerization step is preferably 0.001 parts by mass to 2 parts by mass, more preferably 0.01 parts by mass to 0.5 parts by mass, with respect to 100 parts by mass of the monomer component. When the polymerization initiator is used by at least 0.001 parts by mass, it is possible to reduce the residual monomer. Further, when the polymerization initiator is used by not more than 2 parts by mass, it is possible to restrain a water soluble component in the water absorbent resin.

In the polymerization step of the present invention, the monomer component may be polymerized by being irradiated with active energy beams such as radiation rays, electron beams, ultraviolet rays, or the like, instead of adding the polymerization initiator. In a case where the active energy beams are irradiated, the polymerization initiator may not be added.

The polymerizer to be used in the present invention is preferably a kneader type polymerizer or a belt type polymerizer. A polymerization method that employs the kneader type polymerizer is disclosed in U.S. Pat. No. 6,867,269. In the meantime, the belt type polymerizer includes an endless belt having a dam on its side. The endless belt is made from steel and its surface is coated with fluorine resin. An aqueous solution containing the mixture solution and the polymerization initiator is continuously supplied to the endless belt so as to carry out the aqueous solution polymerization. This method is called a belt polymerization method. Instead of the belt polymerization method, the kneader polymerization method can be employed.

In the present invention, polymerization temperatures (a polymerization-initiation temperature and a maximum temperature during the polymerization) are determined as appropriate depending on a type of the monomer component, a type of the polymerization initiator, and the like, and therefore are not especially limited. However, the temperatures are preferably from 10° C. to 140° C., more preferably 20° C. to 120° C. When the polymerization temperature (polymerization-initiation temperature) is at least 10° C., it is possible to reduce a polymerization time, thereby improving the productivity. Further, when the polymerization temperature (maximum temperature) is not more than 140° C., it is possible to improve properties of a produced water absorbing agent. The polymerization time is also determined as appropriate depending on the type of the monomer component, the type of the polymerization initiator, the temperatures, and the like, and are not especially limited. However, the polymerization time is preferably 0.1 minutes to 10 hours, more preferably 1 minute to 1 hour. Further, the polymerization step may be carried out at normal pressures, under reduced pressures, or under increased pressures.

[Drying Step]

The drying step in the present invention is a step of drying hydrogel prepared in the polymerization step. It is normally preferable that the hydrogel prepared in the polymerization step be subjected to a crushing process so that the hydrogel is crushed into particles around 0.1 mm to 5 mm, and then subjected to the drying step. The drying step can employ various drying methods, for example, methods using a dryer or heating oven, such as hot-air drying and azeotropic dehydration. From the viewpoint of drying efficiency and prevention of deterioration of the hydrogel, the drying step is carried out at preferably 80° C. to 300° C., more preferably 100° C. to 250° C., still more preferably 120° C. to 220° C., especially preferably 150° C. to 200° C. A drying time is not especially limited, and may be determined appropriately so that the resultant polymer has a desired solid content rate. The solid content rate of the polymer prepared in the drying step (i.e., an amount of residues remaining after a heating treatment is carried out at 180° C. for 3 hours) is preferably 90 wt % or more from the viewpoint of easiness in crushing. Generally, although it depends on a particle diameter of the hydrogel, a drying temperature, an air volume, and the like, the drying time is preferably 15 minutes to 2 hours from the viewpoint of production efficiency.

Conventionally, in order to prevent coloring, such a technique is employed that the polymerization conditions and the drying conditions are set moderate (for example, the drying temperature is set relatively low). However, this contributes to an increase in cost and a decrease in productivity. In contrast, according to the present invention, even if the polymerization, drying, and surface crosslinking steps are carried out at high temperatures, it is possible to produce a particulate water absorbing agent having high whiteness with high productivity. That is, the method of the present invention can be preferably applied to a production method for producing a particulate water absorbing agent, which production method includes a drying step like the aforementioned one carried out at 150° C. to 200° C.

[Crushing Step]

The crushing step of the present invention is a step of crushing the hydrogel or the polymer prepared in the drying step. By carrying out the crushing, water absorbent resin particles can be obtained. It is preferable that the crushing be carried out so as to produce as many water absorbent resin particles having an intended diameter as possible. The intended diameter is preferably a weight average particle diameter of 200 μm to 800 μm. How to carry out the crushing is not limited in any particular manner, and a conventionally well-known technique can be employed.

[Classification Step]

The classification step of the present invention is a step of classifying the water absorbent resin particles obtained in the crushing step. In the classification step, the water absorbent resin particles are sieved. Through the classification step, it is possible to obtain a desired particulate water absorbing agent by selecting particles having an intended particle diameter (preferably, the weight average particle diameter is 200 μm to 800 μm). How to carry out the classification is not limited in any particular manner, and a conventionally well-known technique can be employed. The weight average particle diameter is measured in accordance with a method disclosed in U.S. Patent Application Publication No. 2006/0204755.

[Surface Crosslinking Step]

The surface crosslinking step of the present invention is a step of crosslinking a vicinity of a surface of the water absorbent resin particle obtained in the classification step, by use of a surface crosslinking agent. The aforementioned water absorbent resin particle has an internal crosslinking structure. However, from the viewpoint of restraining clumping, the water absorbent resin particle is further crosslinked, thereby resulting in that a crosslinking density on its surface or the vicinity of the surface is increased and becomes higher than a crosslinking density inside the water absorbent resin particle. The "surface or the vicinity of the surface" is a portion around a surface layer, generally a portion that is at most several dozens μm from the surface or at most $1/10$ of the particle diameter from the surface. The thickness of the surface or the vicinity of the surface is determined as appropriate depending on purposes.

How to carry out the surface crosslinking in the present invention is not limited in any particular manner, but any one of the following methods can be used, for example:

(1) A method with the use of an organic surface crosslinking agent and/or a water-soluble inorganic surface crosslinking agent;

(2) A method in which a cross-linkable monomer is crosslinked and polymerized on a surface of the water absorbent resin particle (for example, a method disclosed in U.S. Pat. No. 7,201,941); and (3) A method in which a radical crosslinking is carried out by persulfate or the like (for example, a method disclosed in U.S. Pat. No. 4,783,510).

From the viewpoint of the productivity, the crosslinking reaction is preferably promoted by heating or irradiation of radiation rays (preferably, ultraviolet rays disclosed in EP Patent No. 1824910). By carrying out the surface crosslinking with respect to the surface or the vicinity of the surface of the water absorbent resin particle, it is possible that the water absorbent resin particle has excellent absorbency against pressure, i.e., it is possible to increase absorbency under pressures.

The "surface crosslinking" in the present invention indicates that a region in the surface or the vicinity of the surface of the water absorbent resin particle is chemically or physically modified so that the surface or the vicinity of the surface is crosslinked. In a case of the crosslinked partially neutralized polyacrylic acid, for example, the "chemical modification" indicates that the surface crosslinking is carried out by an organic surface crosslinking agent having at least 2 functional groups that can be reacted with a functional group (especially, a carboxyl group) present in the vicinity of a particle surface. The organic surface crosslinking agent may be, for example, polyalcohol, polyglycidyl compounds, polyamine, or the like. As an alternative technique, the surface crosslinking may be carried out by ion bonding of surface carboxyl groups according to, for example, polyvalent metal such as trivalent aluminum. In the present invention, what type of bonding is formed by the surface crosslinking is not limited in any particular manner, and the water absorbent resin particle whose surface or vicinity of the surface is crosslinked becomes a particulate water absorbing agent.

The surface crosslinking agent used in the surface crosslinking step is not especially limited, but is preferably: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerin, polyglycerin, 2-butane-1,4-diol, 1,4-butanediol, 1,5-pentanediol, 1,6-hexanediol, 1,2-cyclohexanedimethanol, 1,2-cyclohexanediol, trimethylolpropane, diethanolamine, triethanolamine, polyoxypropylene, oxiethylene-oxypropylene block copolymers, pentaerythritol, and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds such as ethylenediamine, diethylenetriamine, triethylenetetramine, tetraethylenepentamine, pentaethylenehexamine, and polyethyleneimine, and inorganic salts or organic salts (for example, aziridinium salt) thereof; polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxane-2-one, 4-methyl-1,3-dioxane-2-one, 4,6-dimethyl-1,3-dioxane-2-one, and 1,3-dioxopane-2-one; haloepoxy compounds such as epicholorohydrin, epibromhydrin, and α-methyl epichlorohydrin; compounds (for example, hydroxide, chloride, and the like) of polyvalent metal such as zinc, calcium, magnesium, aluminum, iron, and zirconium; oxazolidinone compounds such as 2-oxazolidinone (exemplified in U.S. Pat. No. 6,559,239); oxetane compounds; cyclic urea compounds; and the like. Among these compounds, the polyhydric alcohol compounds, the epoxy compounds, the polyamine compounds (and salts thereof), the alkylene carbonate compounds and the oxazolidinone compounds are preferable. At least two types of the surface crosslinking agents may be used in combination.

An amount of the surface crosslinking agent to be used is preferably 0.001 parts by mass to 10 parts by mass, more preferably 0.01 parts by mass to 5 parts by mass, with respect to 100 parts by mass of a solid content of the polymer (the water absorbent resin particle). By setting the amount of the surface crosslinking agent to fall within the range, it is possible to increase the crosslinking density in the vicinity of the surface of the water absorbent resin particle so that it becomes higher than the crosslinking density inside the water absorbent resin particle. Further, such a case where the amount of the surface crosslinking agent exceeds 10 parts by mass is not preferable because it is uneconomic. Moreover, such a case where the amount of the surface crosslinking agent is less than 0.001 parts by mass is also not preferable from the viewpoint of improving properties of the water absorbing agent, such as the absorbency against pressure. This is because a sufficient improvement result cannot be obtained.

In the surface crosslinking step, in order to mix the water absorbent resin particles with the surface crosslinking agent, it is preferable to use water as a solvent. An amount of the water to be used depends on types of the water absorbent resin particle, a particle diameter of the water absorbent resin particle, a moisture content, and the like, but is preferably 0.01 parts by mass to 20 parts by mass, more preferably 0.5 parts by mass to 10 parts by mass, with respect to 100 parts by mass of a solid content of the water absorbent resin particles. Further, a hydrophilic organic solvent may be also added to the aqueous solution as needed. Examples of the hydrophilic organic solvent to be used encompass: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethylformamide; and sulfoxides such as dimethyl sulfoxide. The amount of the hydrophilic organic solvent to be used is preferably not more than 20 parts by mass, more preferably not more than 10 parts by mass, with respect to 100 parts by mass of a solid content of the water absorbent resin particles.

A method for adhering the surface crosslinking agent aqueous solution to the surface of the water absorbent resin particle is not limited in any particular manner, and the following methods, for example, can be employed: a method for spraying the surface crosslinking agent aqueous solution on the surface; and a method for uniformly dropping the surface crosslinking agent aqueous solution onto the surface. In view of adhering the surface crosslinking agent uniformly on the surface, the spraying method is preferable. An average particle diameter of droplets to be sprayed is preferably 0.1 μm to 300 μm, more preferably 0.1 μm to 200 μm.

The reaction between the surface crosslinking agent and the water absorbent resin particles may be carried out at room temperatures or high temperatures. However, it is preferable that the reaction be carried out at high temperatures. In the present invention, a process of carrying out a reaction at high temperatures is referred to as a heating treatment. An atmospheric temperature during the heating treatment is not especially limited, but is preferably 80° C. to 250° C., more preferably 100° C. to 250° C., especially preferably 150° C. to 250° C. By setting the atmospheric temperature during the heating treatment to fall within the range, it is possible to carry out the surface crosslinking uniformly and to ensure high productivity. Furthermore, it is also possible to prevent deterioration of the water absorbent resin particles. A heating treatment time is preferably 1 minute to 2 hours. The heating treatment may be carried out while the particles are being left to stand or while the particles are stirred.

Conventionally, in order to prevent coloring, such a technique is employed that the drying conditions and the surface crosslinking conditions are set moderate (for example, temperatures during the surface crosslinking are set relatively low). However, this contributes to an increase in cost and a decrease in productivity. In contrast, according to the present invention, even if the polymerization, drying, and surface crosslinking steps are carried out at high temperatures, it is possible to produce a particulate water absorbing agent having high whiteness with high productivity. That is, the method of the present invention can be preferably applied to a production method for producing a particulate water absorbing agent, which production method includes a heating treatment like the aforementioned one carried out at 150° C. to 200° C.

[Cooling Step]

The cooling step of the present invention is a step optionally carried out after the surface crosslinking step. More specifically, the cooling step is a step of, for example, cooling down the particulate water absorbing agent that has been subject to the surface crosslinking step so that the vicinity of the surface of the particulate water absorbing agent is crosslinked. A cooling device used in the cooling step is not especially limited, but may be, for example, a biaxial stirring dryer in which cooling water flows through its internal walls and insides of other heat conductive surfaces.

[Additive Addition Step]

In the present invention, an addition step for adding, to the water absorbent resin particles, a modifying agent (additive) other than the surface crosslinking agent may be optionally carried out. The addition step is carried out preferably after the polymerization step, more preferably after the drying step. The additive may be added in the cooling step or other steps. Examples of the additive encompass (A) a deodorant component, (B) polyvalent metal salt, (C) inorganic particles (including (D) composite hydrous oxide particles), (E) a chelating agent, and (F) other additives. The addition of the additive(s) gives various properties to the water absorbing agent.

(A) Deodorant Component

For odor eliminating, the particulate water absorbing agent produced by the production method of the present invention may contain a deodorant component, preferably a plant component. The plant component is preferably one or at least two types of compounds selected from polyphenols, flavones, and caffeine. Among them, one or at least two compounds selected from tannin, tannin acid, Chinese gull, gallnuts, and gallic acid are especially preferable. Further, other plant components may be also added to the particulate water absorbing agent. Examples of the other plant components encompass, for example, theaceous plant-derived components of camellia, eurya, ternstroemia, and the like; gramineae plant-derived components of rice, bamboo grass, bamboo, corn, oats, and the like; rubiaceous plant-derived components of coffee and the like. The plant component to be used may be a plant essence (essential oil) extracted from a plant or the plant itself. Further, plant lees or extraction lees by-produced during production processes in the plant processing industry and the food processing industry may be used as the additive.

(B) Polyvalent Metal Salt

For the purpose of improving liquid permeability and fluidity of the water absorbent resin particles, the particulate water absorbing agent produced by the production method of the present invention may contain polyvalent metal salt. The optional addition of the polyvalent metal salt can restrain blocking when the water absorbent resin particles absorb moisture.

Examples of the polyvalent metal salt encompass polyvalent metal salts of organic acids and inorganic polyvalent metal salts. Preferred examples of the inorganic polyvalent metal salts are, for example, aluminum chloride, polyaluminum chloride, aluminum sulfate, aluminum nitrate, bis potassium aluminum sulfate, bis sodium aluminum sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, zirconium nitrate, and the like. Among these inorganic polyvalent metal salts, aluminum compounds (aluminum chloride, polyaluminum chloride, aluminum sulfate, aluminum nitrate, bis potassium aluminum sulfate, bis sodium aluminum sulfate, potassium alum, ammonium alum, sodium alum, sodium aluminate, and the like) are preferable, and the aluminum sulfate is especially preferable. Further, hydrated crystal powder of aluminum sulfate 18-hydrate, aluminum sulfate 14-18 hydrate or the like can be most preferably used. The polyvalent metal salts may be used solely or at least two types of them may be used in combination. From the viewpoint of a handling ability and miscibility with the particulate water absorbing agent, the polyvalent metal salt is used preferably in a form of solution, especially preferably in a form of aqueous solution.

Further, examples of the polyvalent metal salts of organic acids are disclosed in, for example, U.S. Pat. No. 7,282,262 and U.S. Patent Application Publication No. 2006/0073969. The polyvalent metal salts of organic salt to be used in the present invention are preferably polyvalent metal salts having at least 7 carbon atoms in its molecule. Among them, long chain fatty acid having at least 12 carbon atoms and no unsaturated bond is especially preferable. Examples of the fatty acid encompass lauric acid, myristic acid, palmitic acid, and stearic acid.

The polyvalent metal salt is preferably granulous. From the viewpoint of miscibility, the polyvalent metal salt is preferably a polyvalent metal salt having a particle diameter smaller than that of the water absorbent resin particle. A weight average particle diameter of the polyvalent metal salt is preferably not more than 500 μm, more preferably not more than 400 μm. A ratio of particles having a diameter of not more than 150 μm that are contained in the polyvalent metal salt is preferably not less than 20 mass %, more preferably 30 mass %.

The polyvalent metal salt is mixed with the water absorbent resin particles, preferably in the form of aqueous solution. When a high-concentration aqueous solution is used, it is possible to restrain that polyvalent metal ions are permeated and dispersed inside the water absorbent resin particles. From this viewpoint, with respect to the saturated concentration, the aqueous solution has a concentration of preferably not less than 50%, more preferably not less than 60%, still more preferably not less than 70%, further still more preferably not less than 80%, especially preferably not less than 90%. An aqueous solution having the saturated concentration may be used.

(C) Inorganic Particles

In order to prevent blocking in moisture absorption, inorganic particles, particularly water-insoluble inorganic particles may be added to the particulate water absorbing agent produced by the production method of the present invention. The inorganic particles to be used in the present invention are not especially limited. Examples of the inorganic particles encompass: metal oxides such as silicon dioxide and titanium oxide; silicic acid such as natural zeolite and synthetic zeolite, and salt thereof; kaolin; talc; clay; bentonite and the like. Among them, particles of the silicon dioxide and the silicic acid (silicate) are more preferred, and the silicon dioxide and the silicic acid (silicate) each having an average particle diameter of 0.001 μm to 200 μm as measured by a Coulter counter method are still more preferred.

(D) Composite Hydrous Oxide Particles

The inorganic particles may include composite hydrous oxide. Particles of the composite hydrous oxide increase fluidity and a deodorizing property of the particulate water absorbing agent. The composite hydrous oxide to be used in the present invention may be, for example, a composite hydrous oxide including zinc and silicon, a composite hydrous oxide including zinc and aluminum, or the like.

(E) Chelating Agent

The water absorbing agent produced by the production method of the present invention may contain a chelating agent. The addition of the chelating agent improves absorption capacities of the water absorbing agent with respect to body fluids such as urine. The chelating agent is not especially limited, and a polymer chelating agent and a non-polymer chelating agent can be used. An acid group-containing non-polymer chelating agent is preferred. The acid group-containing non-polymer chelating agent has preferably 2 to 100 acid groups, more preferably 2 to 50 acid groups, especially preferably 2 to 10 acid groups. Examples of the acid group are preferably a phosphoric acid group and a carboxylic acid group. Among them, amino carboxylic acid chelating agents having nitrogen in molecules or amino phosphoric acid chelating agents having nitrogen in molecules are preferred. Preferred examples of the chelating agent encompass: aminocarboxylic acid metallic chelating agents such as iminodiacetic acid, hydroxyethyl iminodiacetic acid, nitrilotriacetic acid, nitrilotripropionic acid, ethylenediamine tetraacetic acid, hydroxyethylenediamine triacetic acid, hexamethylenediamine tetraacetic acid, diethylenetriamine pentaacetic acid, triethylenetetramine hexaacetic acid, trans-1,2-diaminocyclohexane tetraacetic acid, bis(2-hydroxyethyl)glycine, diaminopropanol tetraacetic acid, ethylenediamine-2-propionic acid, glycoletherdiamine tetraacetic acid, bis(2-hydroxybenzyl)ethylenediamine diacetic acid, and salts thereof; phosphorous compounds such as ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphonic acid, nitrilotris(methylenephosphonic acid), cyclohexanediamine tetra(methylenephosphonic acid), ethylenediamine-N,N'-diacetic acid-N,N'-di(methylenephosphonic acid), ethylenediamine-N,N'-di(methylenephosphonic acid), ethylenediamine tetra(methylenephosphonic acid), polymethylenediamine tetra(methylenephosphonic acid), diethylenetriamine penta(methylenephosphonic acid), 1-hydroxyethylidene diphosphonic acid, and salts thereof. The chelating agent may be added to a monomer or a monomer solution.

(F) Other Additive

Optionally added to the water absorbent resin particles may be additives such as disinfectant, an antibacterial agent, fragrant materials, a foaming agent, a pigment, a dye, hydrophilic discontinuous fibers, fertilizer, an oxidizing agent, a reducing agent, aqueous salts, and the like, as necessary.

Respective amounts of the additives to be used are determined depending on purpose and types of the additives. Normally, each of the additives is used by preferably not more than 10 parts by mass, more preferably from 0.0001 parts by mass to 5 parts by mass, especially preferably from 0.002 parts by mass to 3 parts by mass, with respect to 100 parts by mass of a solid content of the polymer (the water absorbent resin particle). In a case where the chelating agent is added, each of the additives is used by preferably not less than 0.0005 parts by mass, more preferably not less than 0.001 parts by mass, still more preferably not less than 0.05 parts by mass, especially preferably 0.1 parts by mass, with respect to 100 parts by mass of the water absorbent resin particle. In this case, an amount of the chelating agent is preferably not more than 1.0 part by mass, more preferably not more than 0.5 parts by mass, especially preferably not more than 0.2 parts by mass.

From the viewpoint of the liquid permeability, polymer polyamine and the polyvalent metal salt (B) are preferably used as the additives. Especially, the polyvalent metal salt (B) is preferred. After the polyvalent metal salt (B) is added, it is preferable that the polyvalent metal salt (B) be mixed with the water absorbent resin particles. Examples of a device for mixing them encompass a cylindrical mixer, a screw mixer, a screw extruder, a turbulizer, a Nautar mixer, a V-shaped mixer, a ribbon mixer, a double-arm kneader, a fluid type mixer, an airflow mixer, a rotary disc type mixer, a roll mixer, a rolling type mixer, and a Lodige mixer.

The particulate water absorbing agent obtained through the above steps is optionally subjected to processes such as granulation, pelletization, and the like, as needed. The resultant particulate water absorbing agent is used for absorbing articles. Examples of the absorbing articles are disposable diapers, sanitary napkins, incontinence pads, and the like.

The particulate water absorbing agent produced by the production method according to the present invention has excellent whiteness because the X value found according to the aforementioned expression (1) is controlled to be not more than 200. Accordingly, in a case where the particulate water absorbing agent is used for the absorbing articles, a user of the absorbing articles feels less uncomfortable.

The particulate water absorbing agent produced in the present invention has a Hunter brightness of preferably not less than 70, more preferably not less than 80, further preferably not less than 90. It is preferable that the particulate water absorbing agent have a larger Hunter brightness. Normally, the produced water absorbing agent has a Hunter brightness of not more than 99. The Hunter brightness conforms to "JIS Z 8719 (2004)", and is found out by measuring an L value, an a value, and a b value.

From a hygiene viewpoint, an amount of a residual monomer in the particulate water absorbing agent is preferably not more than 500 ppm, more preferably not more than 300 ppm, still more preferably not more than 100 ppm. The amount of the residual monomer is measured as follows. Initially, 1000 g of deionized water is measured and poured into a plastic container with a cover. Then, 0.5 g of the particulate water absorbing agent is added into the plastic container, and the resultant in the plastic container is stirred for 2 hours. After a given time, the swelled and gelatinized particulate water absorbing agent is filtered via a filter, and a filtrate is obtained. The filtrate is then analyzed by liquid chromatography. Meanwhile, a monomer (acrylic acid) solution having a given concentration is also analyzed in the same manner so as to form an analytical curve. The analytical curve is taken as a general standard. The amount of the residual monomer is then found based on the general standard, in consideration of a dilution ratio of the filtrate.

EXAMPLES

Advantageous effects of the present invention will be made clear by the following examples. However, the present invention should not be narrowly interpreted within the limits of the descriptions of the following examples.

Example 1

An apparatus having the structure illustrated in FIG. 2 was prepared. The apparatus includes a 300-litter neutralization tank. Into the neutralization tank, there were continuously supplied a 70 mass % acrylic acid aqueous solution and a 48.5 mass % sodium hydroxide aqueous solution. These solutions were circulated through the first loop and the second loop, so as to obtain a mixture solution. A supply volume per unit hour of each of the solutions is as follows.

Acrylic Acid Aqueous Solution: 235 kg/h
Sodium Hydroxide Aqueous Solution: 48.0 kg/h The supply volume may vary in some cases. In these cases, a total amount of each of the solutions to be supplied during operation of the neutralization system is divided by operation hours, so as to find the supply volume. The mixture solution in the neutralization tank had a monomer concentration of 62.7 mass % and a neutralization ratio of 25.5 mol %. The mixture solution was supplied from the neutralization system to the polymerization system. Added to the mixture solution were a sodium hydroxide aqueous solution and an internal crosslinking agent at the line mixer. Then, the mixture solution was mixed with a polymerization initiator, and carried to the polymerizer. Just before being poured into the polymerizer, the mixture solution had a monomer concentration of 54.4 mass %, a neutralization ratio of 70.0 mol %, and a temperature of 97° C. The mixture solution was then continuously poured into the polymerizer, which is a belt type polymerizer. The endless belt of the polymerizer was at a temperature from 60° C. to 70° C. The mixture solution was heated in the polymerizer and irradiated with ultraviolet rays, so as to prepare a polymer gel. The polymer gel was then dried and crushed into particles. After that, a mixture solution of 1,4-butanediol, propylene glycol, and water was sprayed on the particles so that surfaces of the particles were crosslinked. Thus, a water absorbing agent was prepared. The water absorbing agent had a Hunter brightness of 90. In this production method, a volume V of the mixture solution present in the neutralization system was 350 kg, a flow volume F per unit hour of the mixture solution to be supplied from the neutralization system to the polymerization system was 283 kg/h, and a contact area of the mixture solution present in the neutralization system with the neutralization system was 16.3 m$^2$.

Comparative Example 1

A supply volume per unit hour of each of the aqueous solutions was set below, and a flow volume F of the mixture solution was set 21.9 kg/h. Other conditions were set the same as in Example 1. Thus, a polymer gel of Comparative Example 1 was prepared. The polymer gel was then subjected to the drying process, the crushing process, and the surface crosslinking process, in the same manner as Example 1. Thus, a water absorbing agent of Comparative Example 1 was prepared. The water absorbing agent had a Hunter brightness of 64.
  Acrylic Acid Aqueous Solution: 18.2 kg/h
  Sodium Hydroxide Aqueous Solution: 3.7 kg/h
In this production method, a volume V of the mixture solution present in the neutralization system was 350 kg, the flow volume F per unit hour of the mixture solution to be supplied from the neutralization system to the polymerization system was 21.9 kg/h, and a contact area of the mixture solution present in the neutralization system with the neutralization system was 16.3 m$^2$.

Example 2

An apparatus having the structure illustrated in FIG. 2 was prepared. The apparatus includes a 4000-litter neutralization tank. Into the neutralization tank, there were continuously added a 50 mass % acrylic acid aqueous solution and a 48.5 mass % sodium hydroxide aqueous solution. These solutions were circulated through the first loop and the second loop, so as to obtain a mixture solution. A supply volume per unit hour of each of the solutions is as follows.
  Acrylic Acid Aqueous Solution: 6077 kg/h
  Sodium Hydroxide Aqueous Solution: 1279 kg/h
The supply volume may vary in some cases. In these cases, a total amount of each of the solutions to be supplied during operation of the neutralization system is divided by operation hours, so as to find the supply volume. The mixture solution in the neutralization tank had a monomer concentration of 45.9 mass % and a neutralization ratio of 36.8 mol %. The mixture solution was supplied from the neutralization system to the polymerization system. Added to the mixture solution were a sodium hydroxide aqueous solution and an internal crosslinking agent at the line mixer. Then, the mixture solution was mixed with a polymerization initiator, and carried to the polymerizer. Just before being poured into the polymerizer, the mixture solution had a monomer concentration of 43.1 mass %, a neutralization ratio of 73.0 mol %, and a temperature of 93° C. The mixture solution was then continuously poured into the polymerizer, which is a belt type polymerizer. The endless belt of the polymerizer was at a temperature from 60° C. to 70° C. The mixture solution was heated in the polymerizer and irradiated with ultraviolet rays, so as to prepare a polymer gel. The polymer gel was then subjected to the drying process, the crushing process, and the surface crosslinking process in the same manner as Example 1, so as to prepare a water absorbing agent of Example 2. The water absorbing agent had a Hunter brightness of 85. In this production method, a volume V of the mixture solution present in the neutralization system was 3680 kg, a flow volume F per unit hour of the mixture solution to be supplied from the neutralization system to the polymerization system was 7356 kg/h, and a contact area of the solution present in the neutralization system with the neutralization system was 122 m$^2$.

Example 3

An apparatus having the structure illustrated in FIG. 1 was prepared. The apparatus includes a 4000-litter neutralization tank. Into the neutralization tank, there were continuously added a 50 mass % acrylic acid aqueous solution and a 48.5 mass % sodium hydroxide aqueous solution. These solutions were then circulated through the first loop, so as to obtain a mixture solution. A supply volume per unit hour of each of the solutions is as follows.
  Acrylic Acid Aqueous Solution: 1790 kg/h
  Sodium Hydroxide Aqueous Solution: 377 kg/h
The supply volume may vary in some cases. In these cases, a total amount of each of the solutions to be supplied during operation of the neutralization system is divided by operation hours, so as to find the supply volume. The mixture solution in the neutralization tank had a monomer concentration of 45.9 mass % and a neutralization ratio of 36.8 mol %. The mixture solution was supplied from the neutralization system to the polymerization system. Added to the mixture solution were a sodium hydroxide aqueous solution and an internal crosslinking agent at the line mixer. Then, the mixture solution was mixed with a polymerization initiator, and carried to the polymerizer. Just before being poured into the polymerizer, the mixture solution had a monomer concentration of 43.1 mass %, a neutralization ratio of 73.0 mol %, and a temperature of 93° C. The mixture solution was then continuously poured into the polymerizer, which is a belt type polymerizer. The endless belt of the polymerizer was at a temperature from 60° C. to 70° C. The mixture solution was heated in the polymerizer and irradiated with ultraviolet rays, so as to prepare a polymer gel. The polymer gel was then dried and crushed into particles. After that, a mixture solution of 1,4-butanediol, propylene glycol, and water was sprayed on the particles so that surfaces of the particles were crosslinked. Thus, a water absorbing agent of Example 3 was prepared. The water absorbing agent had a Hunter brightness of 72. In this production method, a volume V of the mixture solution present in the neutralization system was 3620 kg, a flow volume F per unit hour of the mixture solution to be supplied from the neutralization system to the polymerization system was 2167 kg/h, and a contact area of the mixture solution present in the neutralization system with the neutralization system was 113 m².

Comparative Example 2

A supply volume per unit hour of each of the aqueous solutions was set below, and a flow volume F of the mixture solution was set 1852 kg/h. Other conditions were set the same as in Example 3. Thus, a polymer gel of Comparative Example 3 was prepared. The polymer gel was then subjected to the drying process, the crushing process, and the surface crosslinking process in the same manner as Example 3. Thus, a water absorbing agent of Comparative Example 3 was prepared. The water absorbing agent had a Hunter brightness of 67.

Acrylic Acid Aqueous Solution: 1530 kg/h
Sodium Hydroxide Aqueous Solution: 322 kg/h In this production method, a volume V of the mixture solution present in the neutralization system was 3620 kg, a flow volume F per unit hour of the mixture solution to be supplied from the neutralization system to the polymerization system was 1852 kg/h, and a contact area of the mixture solution present in the neutralization system with the neutralization system was 113 m².

[Evaluation of Whiteness]

These polymer gels were observed with eyes and their degrees of whiteness were graded in accordance with the following evaluation standard.

A: Extremely White
B: White
C: Slightly Colored
D: Colored

The evaluation results are shown in Table 1 as below.

TABLE 1

| Evaluation Results | | | | | | |
|---|---|---|---|---|---|---|
| | | Ex. 1 | Com. Ex. 1 | Ex. 2 | Ex. 3 | Com. Ex. 2 |
| Capacity of Neutralization Tank | [L] | 300 | 300 | 4000 | 4000 | 4000 |
| V | [kg] | 350 | 350 | 3680 | 3620 | 3620 |
| F | [kg/h] | 283 | 21.9 | 7356 | 2167 | 1852 |
| A | [m²] | 16.3 | 16.3 | 122 | 113 | 113 |
| Residence Time | [h] | 1.24 | 16.0 | 0.50 | 1.67 | 1.95 |
| X | | 20.2 | 261 | 61.0 | 189 | 221 |
| Degree of Whiteness | | A | D | A | B | D |

Abbreviation:
Ex. stands for Example.
Com. Ex. stands for Comparative Example.

As shown in Table 1, the polymer gels prepared by the production methods of Examples have higher degrees of whiteness than those of the polymer gels prepared by the production methods of Comparative Examples. From the evaluation results, it is obvious that the present invention has advantages.

In the production method of the present invention, the value X found according to the expression (1) is controlled to be not more than 200. This makes it possible to prepare a water absorbent resin having a Hunter brightness of at least 70, which is excellent in whiteness. In another aspect of the present invention, it is possible to achieve excellent productivity of the water absorbent resin. Further, it is not necessary to use a new color protection agent or raw materials nor to set polymerization conditions and drying conditions to be moderate. That is, the production method of the present invention can be carried out easily and can yield excellent effects.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A water absorbent resin produced by the production method according to the present invention can be suitably applied to sanitary materials such as disposable diapers, sanitary napkins, and incontinence pads. Further, the water absorbent resin can be used for materials for agriculture, civil engineering, and the like.

The invention claimed is:

1. A method for producing a particulate water absorbing agent, said method comprising the steps of:
    (a) circulating, in a neutralization system including a neutralization tank, a mixture solution containing an acid group-containing monomer and salt obtained by a neutralization reaction of the acid-containing monomer with a basic material;
    (b) continuously supplying, to a polymerization system, a part of the mixture solution that is being circulated; and
    (c) polymerizing a monomer component of the mixture solution in the polymerization system,
    the method satisfying a requirement that a value X is not more than 200, the value X being found according to the following expression:

$$X = (V/F) \cdot A$$

wherein V (kg) is a volume of the mixture solution present in the neutralization system, F (kg/h) is a flow volume of the mixture solution to be supplied to the polymerization system, and A(m²) is a contact area of the mixture solution present in the neutralization system with a device(s) and a pipe(s) constituting the neutralization system.

2. The method as set forth in claim 1, wherein:
    a residence time (V/F) of the mixture solution in the neutralization system is not more than 10 hours.

3. The method as set forth in claim 1, wherein:
    the flow volume F is not less than 100 kg/h.

4. The method as set forth in claim 1, wherein the mixture solution in the neutralization tank has a monomer concentration of 30 mass % to 70 mass %.

5. The method as set forth in claim 1, further comprising, between the steps (b) and (c), the step of:
    (d) adding a basic material to the mixture solution so as to increase a neutralization ratio of the mixture solution.

6. The method as set forth in claim 5, wherein the mixture solution has a neutralization ratio of 30 mol % to 90 mol % right after the step (d).

7. The method as set forth in claim 1, wherein the mixture solution in the neutralization system is circulated through the neutralization tank and a closed flow channel attached to the neutralization tank.

8. The method as set forth in claim 1, wherein:
    the neutralization system includes the neutralization tank, a first loop, and a second loop;
    the mixture solution in the neutralization tank is circulated through the first loop;

the mixture solution is drawn from the neutralization tank or the first loop into the second loop so that the mixture solution is carried through the second loop to a place closer to the polymerization system than to the first loop; and the mixture solution then returns back through the second loop to the neutralization tank or the first loop.

9. A method for producing a water absorbent resin, said method comprising the steps of:
(1) in a neutralization system including a neutralization tank, a first loop, and a second loop, circulating through the first loop a mixture solution which is present in the neutralization tank and which contains an acid group-containing monomer and salt obtained by a neutralization reaction of the acid group-containing monomer with a basic material;
(2) causing the mixture solution to be drawn from the neutralization tank or the first loop into the second loop so that the mixture solution is carried through the second loop to a place closer to a polymerization system than to the first loop, and then causing the mixture solution to return back through the second loop to the neutralization tank or the first loop; and
(3) continuously supplying the mixture solution from the neutralization system to the polymerization system.

10. The method as set forth in claim 1, wherein the acid group-containing monomer is acrylic acid and the acrylic acid contains a polymerization inhibitor by 1 ppm to 200 ppm.

11. The method as set forth in claim 1, wherein:
the acid group-containing monomer is acrylic acid;
the acrylic acid is purified by crystallization or distillation; and
the acrylic acid is then supplied to the neutralization system within 96 hours after the purification.

12. The method as set forth in claim 1, wherein:
the acid group-containing monomer is acrylic acid; and
the neutralization system is connected to a production facility of the acrylic acid via a pipe.

13. The method as set forth in claim 1, wherein the polymerization system carries out continuous kneader polymerization or continuous belt polymerization.

14. A production apparatus for producing a water absorbent resin, said production apparatus comprising:
a neutralization system;
a polymerization system; and
a pipe connecting the neutralization system to the polymerization system,
the neutralization system including:
a neutralization tank in which to store a mixture solution containing an acid group-containing monomer and salt obtained by a neutralization reaction of the acid group-containing monomer with a basic material;
a first loop for drawing the mixture solution from the neutralization tank and for returning the mixture solution back to the neutralization tank; and a second loop for drawing the mixture solution from the neutralization tank or the first loop so that the mixture solution is carried through the second loop to a place closer to the polymerization system than to the first loop, and for returning the mixture solution back to the neutralization tank or the first loop,
the mixture solution being continuously supplied from the neutralization system to the polymerization system via the pipe,
said production apparatus satisfying a requirement that a value X is not more than 200, the value X being found according to the following expression:

$$X=(V/F) \cdot A$$

wherein V (kg) is a volume of the mixture solution present in the neutralization system, F (kg/h) is a flow volume of the mixture solution to be supplied to the polymerization system, and A(m$^2$) is a contact area of the mixture solution present in the neutralization system with a device(s) and a pipe(s) constituting the neutralization system.

15. The production apparatus as set forth in claim 14, wherein the acid group-containing monomer and a mixture solution of the basic material and water are continuously supplied to the first loop.

16. The production apparatus as set forth in claim 14, wherein:
a headspace in the neutralization tank has a volume of 50% to 90% with respect to a volume of the neutralization tank; and
the headspace is sealed with mixed gas of oxygen and inactive gas in which mixed gas an oxygen concentration is adjusted in advance.

17. The production apparatus as set forth in claim 14, wherein the neutralization system further includes a pipe that is connected to a production facility of the acid group-containing monomer.

18. The method as set forth in claim 9, wherein the acid group-containing monomer is acrylic acid and the acrylic acid contains a polymerization inhibitor by 1 ppm to 200 ppm.

19. The method as set forth in claim 9, wherein:
the acid group-containing monomer is acrylic acid;
the acrylic acid is purified by crystallization or distillation; and
the acrylic acid is then supplied to the neutralization system within 96 hours after the purification.

20. The method as set forth in claim 9, wherein:
the acid group-containing monomer is acrylic acid; and
the neutralization system is connected to a production facility of the acrylic acid via a pipe.

21. The method as set forth in claim 9, wherein the polymerization system carries out continuous kneader polymerization or continuous belt polymerization.

* * * * *